(12) United States Patent
Yoda et al.

(10) Patent No.: US 6,407,808 B2
(45) Date of Patent: Jun. 18, 2002

(54) PATTERN INSPECTING SYSTEM AND PATTERN INSPECTING METHOD

(75) Inventors: Haruo Yoda, Nishitama-gun; Mari Nozoe, Oume, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/764,450

(22) Filed: Jan. 19, 2001

Related U.S. Application Data

(63) Continuation of application No. 09/110,343, filed on Jul. 6, 1998, now Pat. No. 6,246,472.

(30) Foreign Application Priority Data

Jul. 4, 1997 (JP) ............................................. 9-179305

(51) Int. Cl.⁷ .............................................. G01N 21/00
(52) U.S. Cl. ................................ 356/237.2; 356/237.3; 356/394
(58) Field of Search .......................... 356/237.1, 237.2, 356/237.3, 237.4, 237.5, 394; 250/559.39, 559.41, 559.45; 382/149, 159; 348/126

(56) References Cited

U.S. PATENT DOCUMENTS

| 5,335,293 | A | * | 8/1994 | Vannelli et al. ................ 382/17 |
| 5,544,256 | A | * | 8/1996 | Brecher et al. ............. 382/149 |
| 5,654,632 | A | * | 8/1997 | Ohno ....................... 324/158.1 |
| 6,092,059 | A | * | 7/2000 | Straforini et al. ............. 706/14 |
| 6,246,472 | B1 | * | 6/2001 | Yoda et al. ............... 356/237.2 |

FOREIGN PATENT DOCUMENTS

JP           60158641        *  8/1985

\* cited by examiner

Primary Examiner—Hoa Q. Pham
(74) Attorney, Agent, or Firm—Kenyon & Kenyon

(57) ABSTRACT

A visual reinspection of circuit patterns using a reviewing apparatus is omitted from a semiconductor circuit pattern forming process to achieve the minute analysis of detected defects in the circuit patterns quickly. A fast pattern inspecting system comprises a calculating means for calculating the graphical characteristic quantities of the defects in synchronism with the detection of the defects, and a classifying means for classifying the defects in clusters by the calculated characteristic quantities.

1 Claim, 8 Drawing Sheets

FIG. 7

| DEFECT NO. | AB-SCISSA | ORDI-NATE | X-SIZE | Y-SIZE | AREA | PERIM-ETER | DEFECT DENSITY | NON-DEFECTIVE PART DENSITY | NONDEFECTIVE PART DIFFERENTIAL DENSITY | DENSITY DIFFERENCE | DESIGN DATA |
|---|---|---|---|---|---|---|---|---|---|---|---|
| 1 | | | | | | | | | | | |
| 2 | | | | | | | | | | | |
| 3 | | | | | | | | | | | |
| 4 | | | | | | | | | | | |
| 5 | | | | | | | | | | | |
| 6 | | | | | | | | | | | |

MAP OF DEFECTIVE WAFER

○ ··· CLUSTER 1
△ ··· CLUSTER 2
× ··· CLUSTER 3

MAP OF DEFECTIVE CHIP

○ ··· CLUSTER 1
△ ··· CLUSTER 2
× ··· CLUSTER 3

PATTERN INSPECTING SYSTEM AND PATTERN INSPECTING METHOD

This is a continuation of U.S. patent application Ser. No. 09/110,343, filed Jul. 6, 1998, now U.S. Pat. No. 6,246,472.

FIELD OF THE INVENTION

The present invention relates to a pattern inspecting system for detecting defects in an array of the same patterns arranged at a predetermined pitch on a surface of a workpiece and, more particularly, to a pattern inspecting system suitable for inspecting the appearance of semiconductor patterns formed on a surface of a wafer.

BACKGROUND OF THE INVENTION

When fabricating a semiconductor integrated circuit, such as a large-scale integrated circuit, it is important to detect defects formed in patterns in pattern forming processes and to eliminate the causes of the defects for the improvement of the yield of a semiconductor integrated circuit fabricating system including the pattern forming processes.

The inventors of the present invention proposed a pattern inspecting system capable of automatically detecting defects in semiconductor patterns in Japanese Patent Laid-open No. 59-192943 and this previously proposed pattern inspecting system has been practically used. Principles on which the previously proposed pattern inspecting system is based will be explained. A workpiece, i.e., a semiconductor wafer, is fixedly mounted on a constant-speed movable sample table. The workpiece is moved at a constant speed while a linear sensor disposed perpendicularly to the direction of movement of the workpiece scans the surface of the workpiece and produces image signals. Usually, the same patterns are formed at a predetermined pitch on a semiconductor wafer and, therefore, image signals of the same waveform are produced repeatedly. The image signals are compared with image signals delayed by a time corresponding to the pitch of the patterns. The difference between the image signals is large for parts of the patterns including defects.

The pattern inspecting system based on this principle is capable of detecting defects at a very high defect detecting rate as compared a defect detecting rate at which an operator is able to detect defects. Therefore, the pattern inspecting system has been practically used on semiconductor integrated circuit producing lines as an essential inspecting system. This defect detecting device, however, provides the coordinates of defects as principal defect information. Therefore, it has been necessary to inspect every detected defect visually by means of a reviewing apparatus with reference to a list of the coordinates of the defects provided by the pattern inspecting system to specify the causes of the defects.

Thus the prior art requires the visual inspection of the defects by means of the reviewing apparatus with reference to the list of the coordinates of the defects provided by the pattern inspecting system to obtain necessary data on the defects. Consequently, much time and labor are necessary in addition to time and labor necessary for detecting the defects by the pattern inspecting system to elucidate the causes of the defects. Furthermore, since the visual inspection of the defects needs much time and labor, it is impossible to inspect visually all the defects detected by the pattern inspecting system and only the general condition of causes of the defects could have been estimated from the results of visual inspection of randomly selected sample defects. Consequently, it has been possible that information about serious defects which are formed at a low probability is overlooked.

SUMMARY OF THE INVENTION

Accordingly, it is an object of the present invention to achieve quickly the minute analysis of detected defects formed in patterns in a semiconductor pattern forming process by omitting the visual inspection of the defects by means of a reviewing apparatus.

With the foregoing object in view, the present invention provides a pattern inspecting system for quickly detecting defects in patterns comprising a calculating means for calculating characteristic quantities representing the graphical characteristics of defects in synchronism with defect detection, and a classifying means for classifying the defects in clusters by calculated characteristic quantity.

The pattern inspecting system is capable of analyzing the defects. Therefore, the causes of simple defects can be specified through simple defect analysis without requiring visual inspection using the reviewing apparatus. Peculiar defects will not be overlooked, the causes of defects can be quickly specified and the foregoing problems in the prior art can be solved by specifying defects which need visual inspection using a reviewing apparatus.

BRIEF DESCRIPTION OF THE INVENTION

Figure 3A:
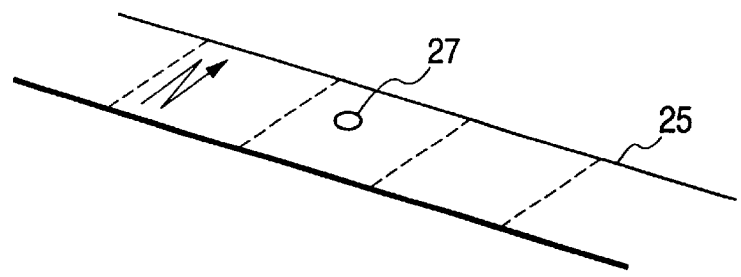
Figure 3B:
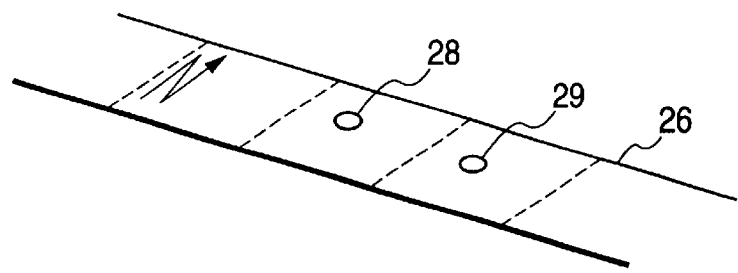
Figure 4:
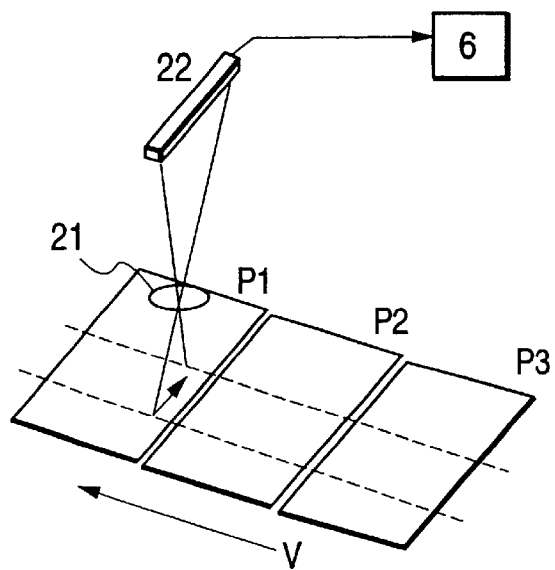
Figure 5A:
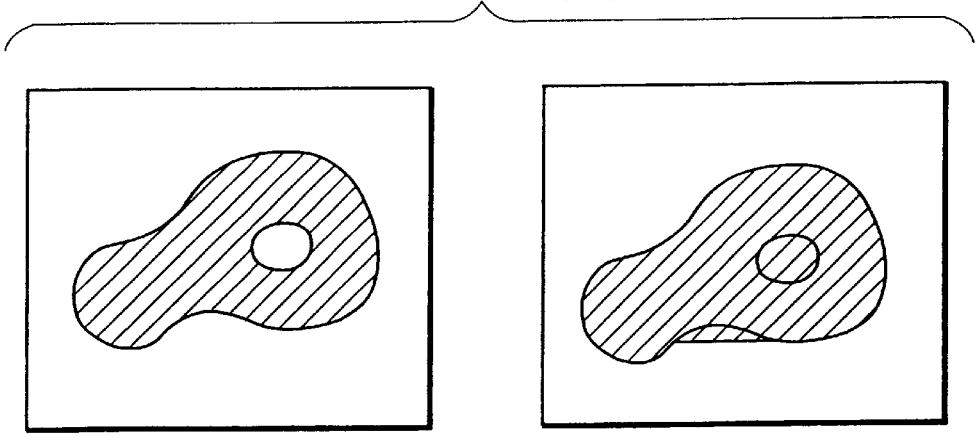
Figure 5B:
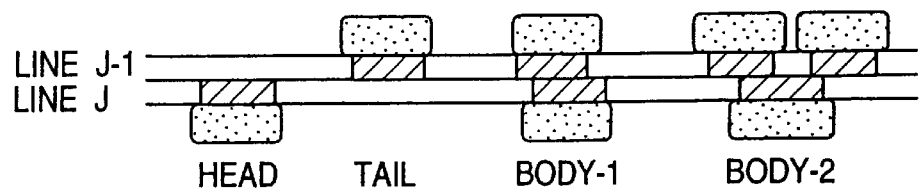
Figure 6:
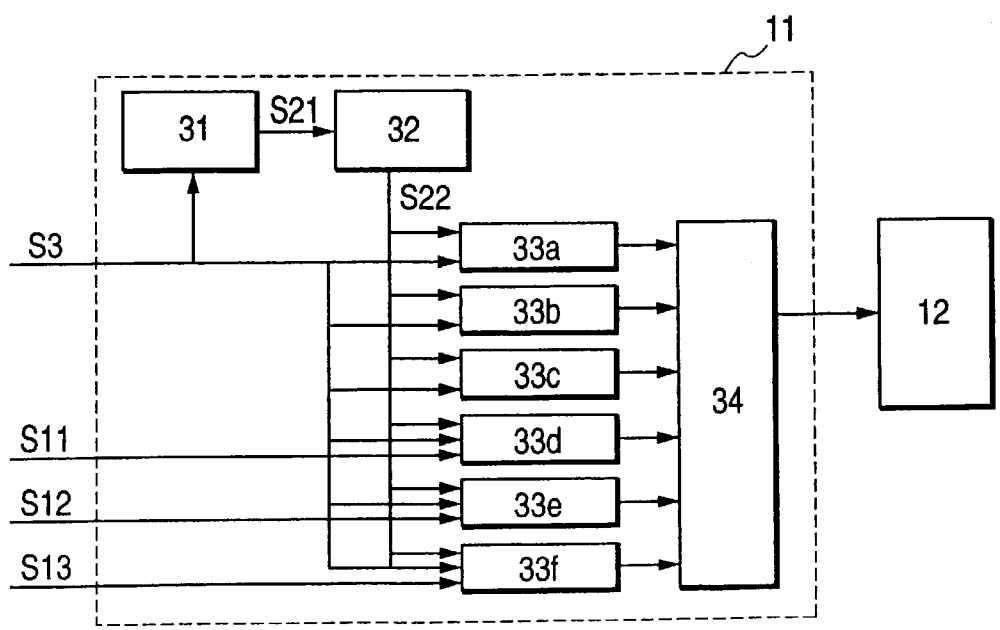
Figure 8A:
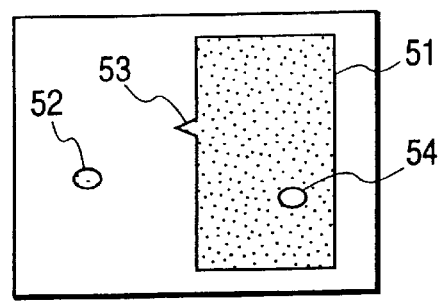
Figure 8B:
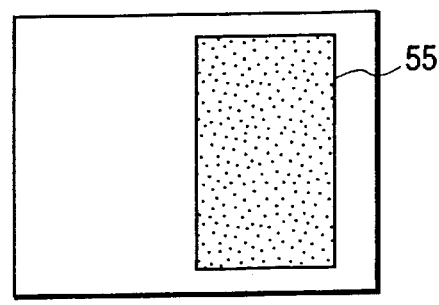
Figure 8C:
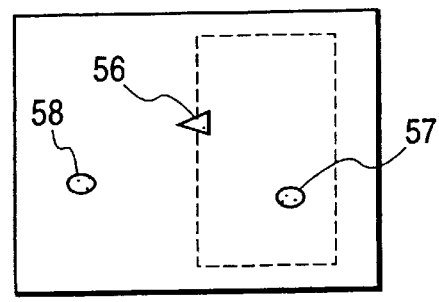
Figure 9A:
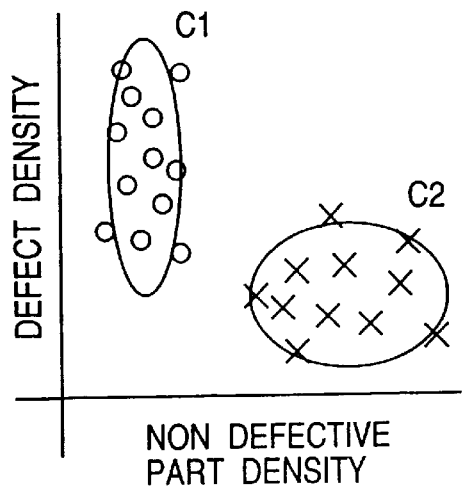
Figure 9B:
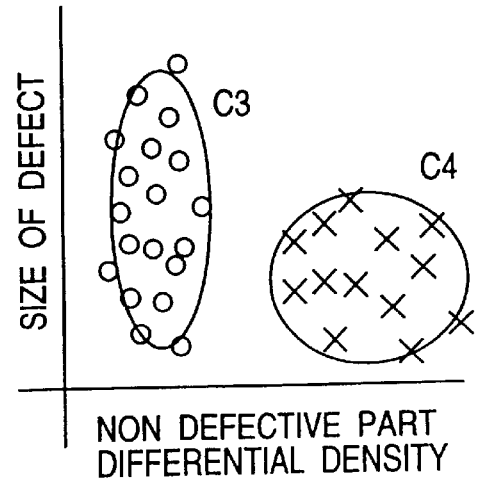
Figure 10A:
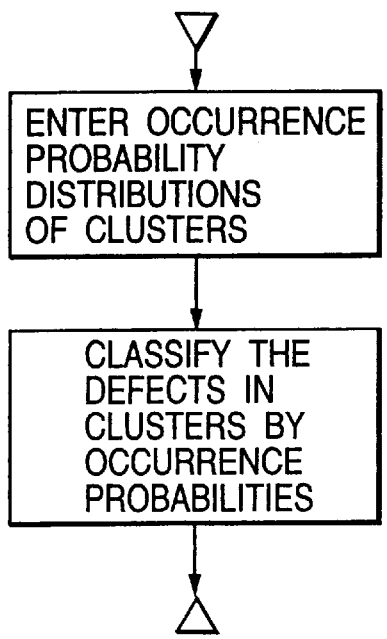
Figure 10B:
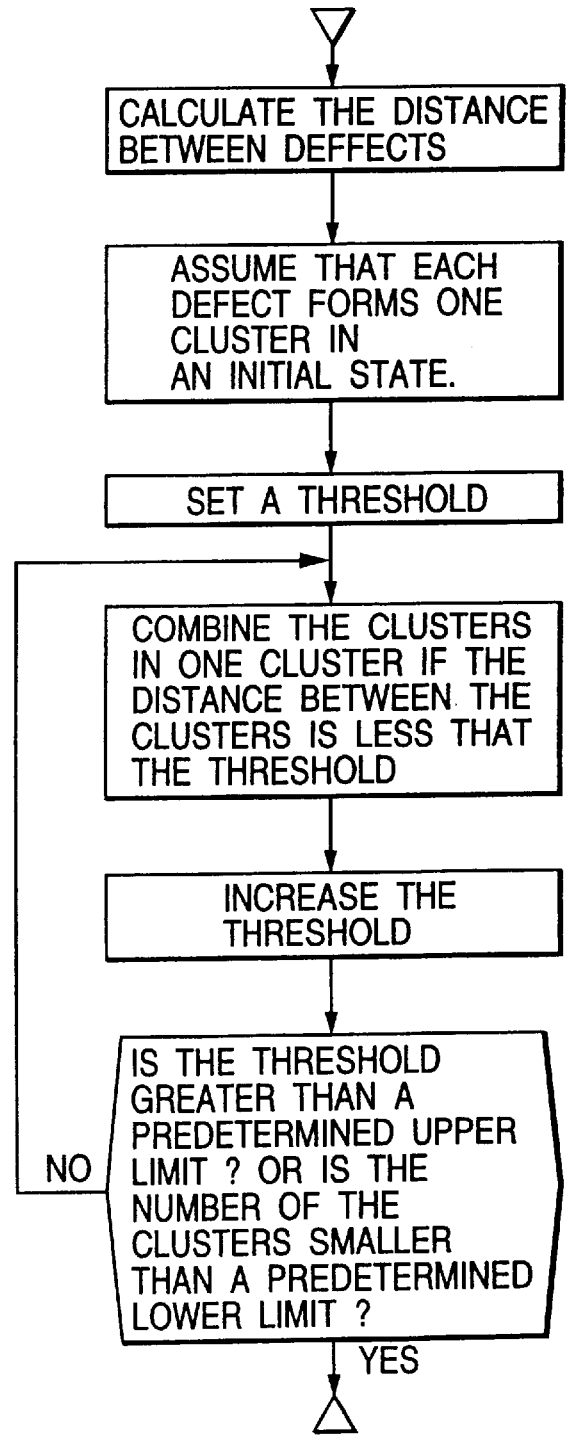
Figure 11A:
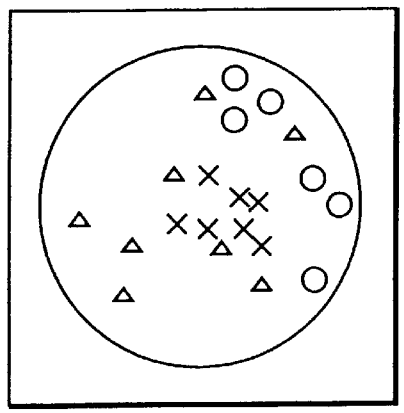
Figure 11B:
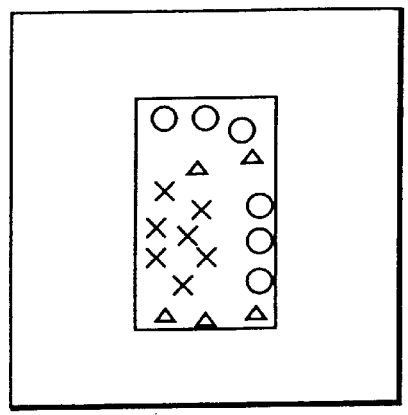
Figure 12:
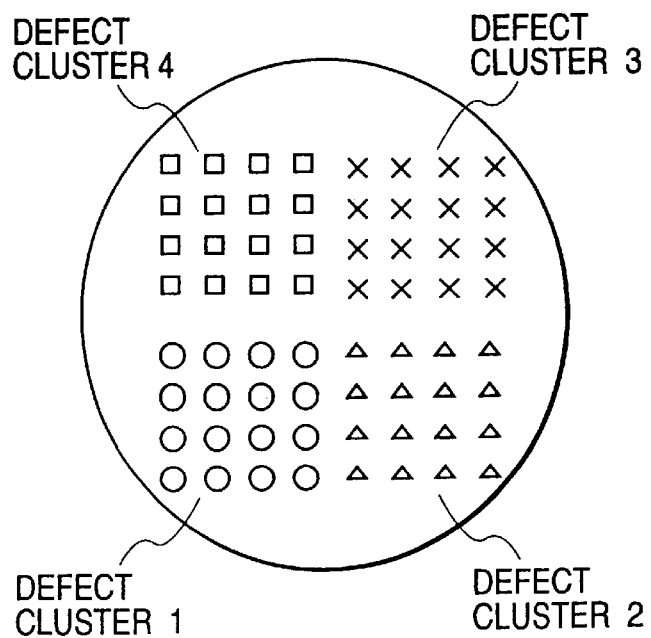
Figure 13:
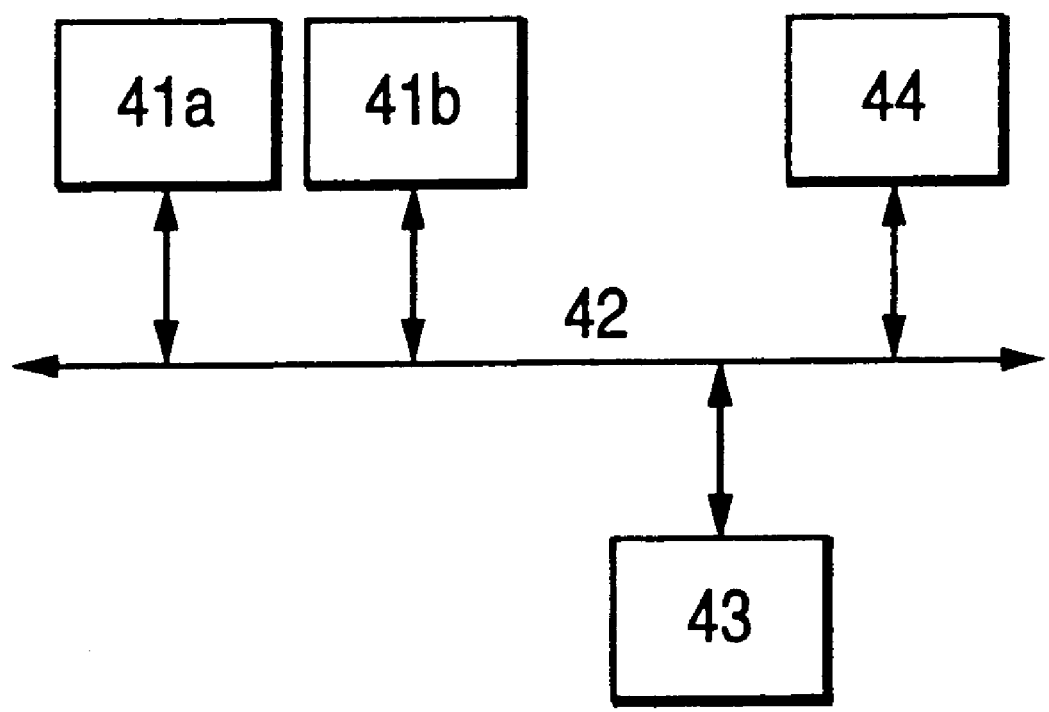

FIGS. 3(a) and 3(b) are perspective views of images represented by image signals of assistance in explaining a defect detecting method;

FIG. 4 is a perspective view of patterns formed on a semiconductor wafer of assistance in explaining an image pickup method using a linear sensor;

FIGS. 5(a) and 5(b) are a plan view and a sectional view, respectively, of images for extracting characteristic quantities of defects;

FIG. 6 is a block diagram of a characteristic quantity calculating circuit;

FIG. 7 is an example of a list of characteristic quantities representing defects;

FIGS. 8(a), 8(b) and 8(c) are plan views of images of detected defects;

FIGS. 9(a) and 9(b) are graphs showing the distributions of defects in a characteristic space;

FIGS. 10(a) and 10(b) are flow charts of a defect classifying procedure;

FIGS. 11(a) and 11(b) are views of images of defect clusters of classified defects;

FIG. 12 is a view of an image of an occurrence probability distribution measuring wafer; and FIG. 13 is a block diagram of pattern inspecting system in a second embodiment according to the present invention.

DETAILED DESCRIPTION OF THE PREFERRED EMBODIMENTS

A known characteristic quantity calculating procedure of calculating characteristic quantities of patterns represented by image data at the same time when the data is input on the basis of rows of image data rapidly and continuously provided by raster scanning is proposed by the inventors of the present invention in Japanese Patent Laid-open No. 63-217479. This characteristic quantity calculating procedure enables a pattern inspecting system to calculate the graphical characteristic quantities of defects without reducing defect detecting rate. Various algorithms for clustering techniques for classifying defects in clusters are known in this technical field. Thus a pattern inspecting system according to the present invention can be easily realized by combining known techniques. The pattern inspecting system of the present invention is characterized by a method of detecting defects by which the pattern inspecting system detects defects.

A defect classifying method may be realized by a defect classifying procedure which classifies defects in clusters by employing a characteristic space defined by coordinate axes on which the characteristic quantities of defective regions are measured, indicating each piece of defect data by a point in the characteristic space, and automatically classifying masses of points into clusters or may be realized by a defect classifying procedure which classifies defects in clusters by measuring the occurrence probabilities of clusters of defects in a characteristic space to obtain known information beforehand, and classifying defects into known defect clusters on the basis of the known information. The former defect classifying procedure is effective in the evaluation of a new semiconductor pattern forming process, and the latter defect classifying procedure is effective in regularly inspecting the same process.

Size, area and perimeter representing a shape are effective characteristic quantities for classyfying defects. Densities of defective regions and those of normal regions are effective data for indicating types of defects and defective regions. Usually, the average density of a region is calculated by calculating the sum of densities of defective regions and normal regions, and is obtained by dividing the sum of densities by the calculated area of the region. The sum or the square sum of the absolute values of the differences between the densities of defective regions and the density of the normal region may be effective data for grading defects.

An image pickup apparatus may be of a type which scans the surface of a workpiece linearly with a fine electron beam or a light beam, and provides a video signal representing the intensities of electron currents or light intensities or may be of a type which irradiates a workpiece with an electron beam or a light beam, projects an electron beam image or an optical image on a sensor array, and provides a video signal by electronically scanning the sensor array. Either of these image pickup apparatus scans the surface of the workpiece linearly to provide the video signal.

Usually, the density of an image used for calculating characteristic quantity representing a defect is a digital image signal obtained by converting the video signal. An image signal different from a digital image signal employed in defect detection may be used. For example, a density obtained by processing an input image signal for spatial smoothing or edge highlighting may be used. A video signal different from a video signal for detecting defects may be used if the pattern inspecting system is provided with an image pickup means capable of simultaneously providing a plurality of video signal. For example, if an electronic microscope capable of providing a secondary electron signal and a reflected electron signal as different video signals is employed as the image pickup apparatus, one of the video signals may be used for detecting defects and the other may be used for calculating the characteristic values of defects. If an optical inspecting system capable of using color information is employed, color components or linear combinations of color components may be used as image density data for calculating characteristic quantities. The use of various image density data for calculating characteristic quantities for classification enables the pattern inspecting system to classify defects in further improved accuracy.

A method of calculating characteristic quantities representing defects based on the areas and sizes of defective regions and a design pattern, and a method of classifying defects on the basis of the calculated characteristic quantities proposed by the inventors of the present invention is mentioned in "An Automatic Wafer Inspection System using Pipelined Image Processing Techniques", IEEE Trans. PAMI, Vol. 10, No. 1, January, 1988. Although this previously proposed method of classifying defects is an effective means for determining the criticality of each defect to enhance the reliability of the pattern inspecting system, the same is not a sufficiently effective means for specifying the causes of defects. A pattern inspecting system according to the present invention comprises a calculating means capable of calculating graphical characteristic quantities on the basis of density information about a defective pattern and a corresponding normal pattern substantially simultaneously with the detection of a defective region, and a classifying means for automatically classifying the detected defects in clusters in a characteristic space, and a display means for displaying the defects classified in cluster, and is capable of quickly determining the causes of the defects.

Figure 1:
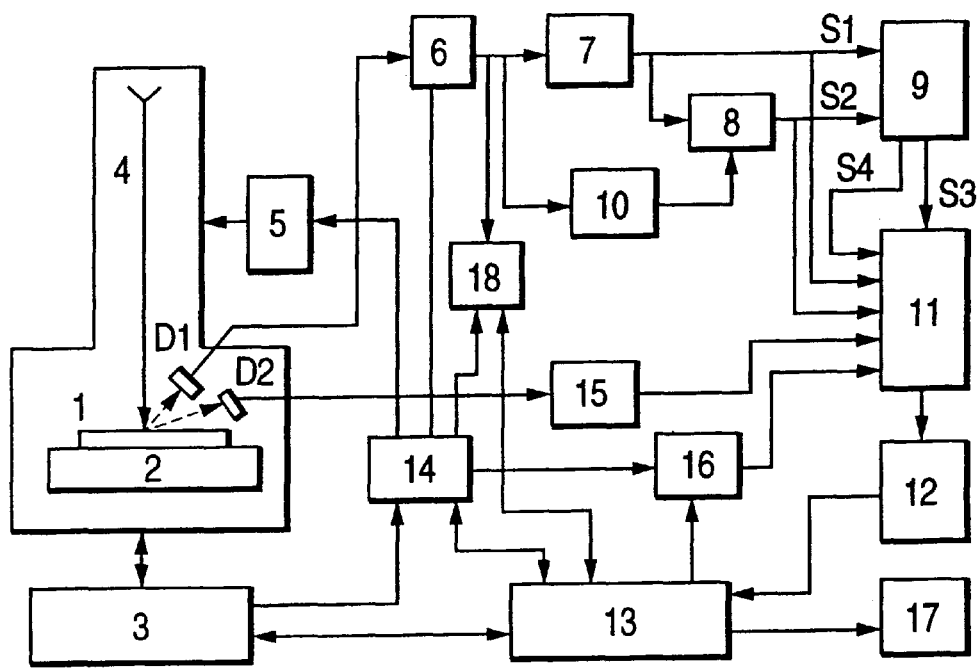
FIG. 1 is a block diagram of a pattern inspecting system in a first embodiment according to the present invention.

FIG. 1 shows a pattern inspecting system in a first embodiment according to the present invention. The pattern inspecting system scans the surface of a workpiece 1, i.e., a semiconductor wafer, with an electron beam and provides a video signal. The workpiece 1 is mounted on a movable sample table 2. Patterns formed on the surface of the workpiece 1 are scanned repeatedly with a fine electron beam 4 along scanning lines intersecting the direction of movement of the sample table 2. A semiconductor sensor D1 senses an electron current produced by the scanning action of the electron beam 4 and gives a video signal representing the patterns formed on the surface of the workpiece 1 to a fast A/D converter 6. Since the workpiece is moving at a constant speed, the video signal assumes an infinitely long raster scan image signal of a fixed width.

Figure 2:
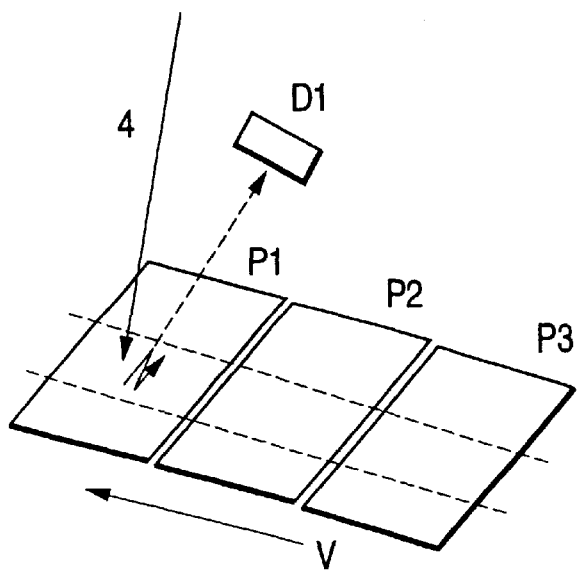
FIG. 2 is a perspective view of patterns formed on a semiconductor wafer of assistance in explaining image formation by electron beam scanning.

FIG. 2 is a perspective view of patterns formed on a surface of a workpiece, i.e., a semiconductor wafer, of assistance in explaining image formation by electron beam scanning. The same patterns P1, P2 and P3 are arranged successively at a predetermined pitch on the surface of the workpiece. When the workpiece is moved at a constant speed while the patterns P1, P2 and P3 are scanned successively with the electron beam 4, the sensor D1 provides video signals of the same waveform at a pitch corresponding to that of the patterns P1, P2 and P3. The A/D converter 6 converts the video signals into corresponding digital signals and gives the digital signals to a delay circuit 7. An output signal S1 provided by the delay circuit 7 is given to a one-pitch delay circuit 8. The output signal S1 of the delay circuit 7 and the output signal S2 of the delay circuit 8 are video signals of the same waveform, and the output signal S2 of the delay circuit 8 is delayed by one pitch behind the output signal S1 of the delay circuit 7. A defect image signal S3 indicating a defective region by "1" can be produced from the difference in intensity between the delayed signals S1 and S2 by minutely comparing the output signals S1 and S2. The processes are carried out in synchronism with the input of all the video signals in a pipelined image processing system for each pixel. Thus, the defect image is a raster scan image delayed by a substantially fixed time behind the input image.

The positional relation between the output signals S1 and S2 must be precisely adjusted to detect the defective region accurately. The positional relation is adjusted by a positional difference detecting circuit 10. The positional difference detecting circuit 10 internally provided with a delay circuit corresponding to the delay circuit 8 determines the positional difference between the output signals S1 and S2 to optimize a lag by which the delay circuit 8 delays the input signal. The delay circuit 7 corrects a time lag between the detection of the positional difference and the adjustment of the delay circuit by the positional difference detecting circuit 10. These principles of defect detection are mentioned in detail in Japanese Patent Laid-open No. 59-192943 and "An Automatic Wafer Inspection System Using Pipelined Image Processing Techniques", IEEE Trans. PAMI, Vol. 10, No. 1, January, 1988. A defect extracting circuit 9 executes many processes for additional operations to compensate the variation of intensity, a positional difference less than one pixel detected by the positional difference detecting circuit 10, for shaping a detected defect image and elimination of noise patterns. Explanation of these process will be omitted to facilitate understanding the present invention.

FIGS. 3(a) and 3(b) are perspective views of images represented by input image signals of assistance in explaining a defect detecting method based on this principle. FIG. 3(a) shows an input image signal 25 representing an infinitely long raster scan image, and a defect 27 included in the infinitely long raster scan image. FIG. 3(b) shows a defect image signal 26 produced by processing the input image signal 25 shown in FIG. 3(a). When the input image includes the defect 27, a defect detection image 28 is provided with a lag. Since an input defect image is used as the output signal S2 representing a reference image at time delayed by a lag corresponding to the pitch of the patterns, a pseudo defect detection image 29 is obtained. These two defect detection image cannot be individually verified. However, since real defects are formed in pairs and separated by a distance corresponding to the pitch of the patterns owing to the construction of a pattern forming apparatus for forming the patterns, only the real defects can be detected by removing the pseudo defects from a final detected defect list according to a fixed rule.

FIG. 4 is a perspective view of patterns formed on a semiconductor wafer of assistance in explaining an image pickup method using a linear sensor. Defect detection may be achieved not only by linearly moving an electron beam or a light beam for scanning but also by detecting an image of a workpiece projected through an optical lens 21 on a linear sensor 22 by the linear sensor 22 as shown in FIG. 4.

The defect image signal S3 provided by the defect extracting circuit 9 shown in FIG. 1 is given to a characteristic quantity calculating circuit 11. The characteristic quantity calculating circuit 11 calculates the position, size and area of each defect on the basis of the defect image signal S3 in a real-time processing mode. According to the present invention, the output signal S1 representing the density of an input image of each defective region, the output signal S2 representing the density of the reference image, and an output signal S4 representing the density of a difference absolute value image are given by sensors other than the sensor for defect detection to the characteristic quantity calculating circuit 11. The characteristic quantity calculating circuit 11 has a function to calculate the sum of the density of a video signal undergone time adjustment carried out by a delay adjusting circuit 15, and a design pattern density provided by a design pattern generating circuit 16 as a characteristic quantity representing a defect.

The characteristic quantity calculating circuit 11 calculates a characteristic quantity of defects on the basis of defect image data obtained by raster scanning according to a fixed pixel clock in a real-time processing mode in synchronism with the input of a defect image every time a defect image appears. This operation of the characteristic quantity calculating circuit 11 is mentioned in detail in Japanese Patent Laid-open No. 63-217479.

The calculated characteristic quantity is stored in a memory 12 every time the calculation is completed, and a control computer 13 reads the characteristic quantity from the memory 12 every time the inspection of one unit region is completed. The control computer 13 controls the general operations of the pattern inspecting system. A table control circuit 3 controls the operation of the sample table 2. A timing signal generating circuit 14 controls the timing of execution of inspecting processes. Pattern data is stored in a design pattern generating circuit 16. An image recognition circuit 18 is controlled by the control computer 13, is internally provided with an image memory to store image data on the position of a specific pattern on the workpiece, and measures the position of the specific pattern on the image precisely through the calculation of the correlation between the image data and a template pattern, i.e., a reference pattern, stored therein beforehand. The difference between the design position of the specific pattern and the measured position of the same is calculated from coordinates indicating the position of the sample table 2 and coordinates of the position of the specific pattern on the workpiece, and the calculated difference is given to the control computer 13.

The timing signal generating circuit 14 controls the deflection of the electron beam 4 deflected by the electron beam deflection control circuit 5, the timing of deflection of the electron beam 4, and the timing of reception of the signals provided by the A/D converter 6 and the design pattern generating circuit 16 on the basis of information provided by the control computer 13, and information about the position of the sample table 2 provided by the table control circuit 3. Practically, the timing signal generating circuit 14 sends the timing signal to other circuit blocks, the description of which is omitted for simplicity. The defect characteristic quantity data given to the control computer 13 is classified by the software of the control computer 13, and the results of classification is displayed on a display unit 17.

Concept of a characteristic quantity calculating method by which the characteristic quantity calculating circuit 11 calculates a characteristic quantity will be explained below. The characteristic quantity calculating method is explained in detail in Japanese Patent Laid-open No. 63-217479. FIGS. 5(a) and 5(b) show images for the extraction of a defect characteristic quantity. FIG. 5(a) shows an input image and FIG. 5(b) shows simplified lines of the input image.

The input image as shown by the left-hand view in FIG. 5(a) is processed by a simple recursive digital filter to produce a control image obtained by filling up upward convex areas and openings included in a binary pattern as shown in the right-hand view in FIG. 5(a). This deformation provides the control image of a simple pattern. As is obvious from image data on two successive raster scanning lines, every pattern includes only four shapes shown in FIG. 5(b). Suppose that the two successive raster scanning lines are a line J and a line J−1. Part of a pattern appears in HEAD for the first time, the pattern terminates in TAIL on the line J−1, a pattern on the line J−1 is connected to the line J in BODY−1, a plurality of patterns on the line J−1 are connected to one pattern on the line J in BODY−2. Although it may be considered that a single pattern on the line J−1 is divided into a plurality of pattern on the line J, the control image produced by deformation does not have any one of them.

Operations for the calculation of characteristic quantity are carried out sequentially on the control image in order of raster scanning. the connection of the two successive raster scanning lines are monitored. If a HEAD shown in FIG. 5(b) appears, a partial characteristic quantity of a part of the image on the line J is stored as an intermediate characteristic quantity of the line J. If a TAIL appears, data stored as an intermediate characteristic quantity of the line J−1 is given as a defect characteristic quantity. If a BODY−1 appears, the intermediate characteristic quantity of the line J−1 is read, is combined with the partial characteristic quantity of the line J, and the result of combination is stored again as an intermediate characteristic quantity of the line J. If a BODY−2 appears, an intermediate characteristic quantity of a corresponding pattern on the line J−1 is synthesized, and is combined with a partial characteristic quantity on the line J, and the result is stored again as an intermediate characteristic quantity of the line J. When this operation is executed in synchronism with the input of each line, the defect characteristic quantity calculation can be achieved substantially simultaneously with the input of image data. The intermediate characteristic quantity of the line J−1 need not be stored after the intermediate characteristic quantity of the line J has been stored and hence a storage circuit for the line J−1 can be used as means for storing the intermediate characteristic quantity of the next line J+1. Thus, only a storage area for two lines is necessary, and the characteristic quantities of all the defects can be calculated without increasing the storage area regardless of the number of the lines.

FIG. 6 is a block diagram showing the configuration of the characteristic quantity calculating circuit 11 in detail. A control image producing circuit 31 processes the defect image signal S3 to produce a control image signal S21. A control signal producing circuit 32 processes the control image signal S21 to produce a control signal S22 for characteristic quantity calculation. Characteristic quantity calculating circuits 33a, 33b, 33c, 33e, 33e and 33f are controlled by the control signal S22 to calculate defect characteristic quantities corresponding to input image data given thereto.

In FIG. 1, six input signals are given to the characteristic quantity calculating circuit 11. In FIG. 6, output signals other than the defect image signal S3 are represented by output signals S11, S12 and S13. The characteristic quantity calculating circuits 33a, 33b and 33c operate the defect image signal S3 to calculate the coordinates, X-size, Y-size and area of a defect. The characteristic quantity calculating circuits 33d, 33e and 33f operates the output signals S11, S123 and S13 to calculate the sum of image densities on the defect image signal S3. The output signals S11, S12 and S13 correspond to the inputs given to the characteristic quantity calculating circuit 11, respectively. Signals obtained by subjecting those signals to filtering, such as spatial differentiation, may be used. Since these operations for characteristic quantity calculation are executed in synchronism with scanning, all the characteristic quantities about the same defect images are provided in the same timing. A critical defect deciding circuit 34 examines the sizes and the area, and gives information about only critical defects together with characteristic quantities to the memory 12. When a pattern formed on a wafer is inspected, many minute pseudo defects which are not critical are detected. Therefore, the function of the critical defect deciding circuit 34 is important to avoid unnecessary information which may cause the memory 12 to easily overflow.

The control computer 13 receives the characteristic quantities corresponding to the sum of densities, and divides the same by the area to provide an average density easy to handle. Finally, the defect characteristic quantities rearranged by the control computer 13 are tabulated in a defect characteristic quantity list as shown in FIG. 7. In the first embodiment, the defect characteristic quantities include abscissas, ordinates, X-sizes, Y-sizes, areas, perimeters, defect densities, nondefective part densities, nondefective part differential densities, density differences and design data. Defect density is obtained by dividing the sum of densities represented by the output signal S1 indicating input image densities in defective region by the area of the defective area. Nondefective part density is obtained by dividing the sum of densities represented by the output signal S2 indicating the density of a reference image by the area. Nondefective part differential density is obtained by dividing the sum of density images equal to the absolute value of the differential of the output signal S1 indicating the density of the input image by area. Density difference is obtained by dividing the sum of the output signal S4 indicating the density of an image from which the absolute value of the accurate difference between the output signals S1 and S2 by area. Design data is obtained by dividing the sum in a defective part in a binary image produced by the design pattern generating circuit 16 so that the interior of the specific pattern is "1" by area. A process of summing up the values of a density image in a defective region is generally called "volume" calculation. All the operations for characteristic quantity calculation including the volume calculation are the same as those mentioned in Japanese Patent Laid-open No. 63-217479.

Data to be used as a design pattern may be automatically produced from pattern data used for forming the pattern on the workpiece, may be produced in an interactive mode by graphic software based on the data on the image of the workpiece or may be produced by subjecting the density of the data on the image of the workpiece to threshold operation.

FIGS. 8(a), 8(b) and 8(c) show images of extracted defects by way of example. FIG. 8(a) shows an input image including a defect, FIG. 8(b) shows a reference image for comparison and FIG. 8(c) shows defects. The input image shown in FIG. 8(a) has a circuit pattern 51 and input defect patterns 52, 53 and 54. When the respective image densities of the interior and the exterior of a pattern 55 in the reference image are different from each other, the internal defect 57 and the external defect 58 can be discriminated from each other if the nondefective part density, i.e., the density of the normal region corresponding to an extracted defect region is used as a characteristic quantity. The defect 56 on the boundary can be discriminated from the internal defect 57 and the external defect 58 by using the nondefective part differential density, i.e., the differential density of the normal region corresponding to the extracted defective region, is used as a characteristic quantity. Various types of defects can be classified in clusters by applying many kinds of characteristic quantities for extracted defects.

FIGS. 9(a) and 9(b) are views of assistance in explaining defect distribution in a characteristic space, in which extracted defects are plotted in the characteristic space defined by coordinate axes on which the characteristic quantities are measured. FIG. 9(a) shows a two-dimensional space defined by an axis on which nondefective part density is measured and an axis on which defect density is measured. It is known from FIG. 9(a) that bright defects on a dark pattern, and dark defects on a bright pattern are classified into clusters C1 and C2, respectively. FIG. 9(b) shows a two-dimensional space defined by an axis on which nondefective part differential density is measured and an axis on which defect size is measured. It is known from FIG. 9(b) that defects on the boundary of a pattern where the density changes, and defects not on the boundary are classified into clusters C4 and C3, respectively. Although not shown in FIGS. 9(a) and 9(b), defects inside a region specified as a design pattern and those outside the same can be classified into clusters by using design data as characteristic quantities.

Thus causes of defects can be analyzed to some extent by classifying detected defects into clusters by characteristic quantity without requiring visual reinspection using a reviewing apparatus. FIGS. 10(a) and 10(b) are flow charts of a procedure for defect clustering. If the occurrence probability distributions of clusters are known, the occurrence distribution functions of the clusters are entered as shown in FIG. 10(a), and defects are classified in clusters having the highest occurrence probability. If the mode of occurrence of each cluster is not known at all, a cluster can be automatically estimated from the condition of a mass of occurred defects in a characteristic space as shown in FIG. 10(b) by the following procedure.

(1) The distance between optional defects in the characteristic space is calculated.

(2) It is assumed that each defect form one cluster in an initial state.

(3) A threshold is set, the clusters are combined in one cluster if the distance between the clusters, i.e., the distance between the nearest defects included in the clusters, is less than the threshold.

(4) The threshold is increased somewhat.

(5) The procedure is ended if the threshold exceeds a predetermined upper limit or the number of the clusters is less than a predetermined lower limit and, if not, (3) is repeated.

Clustering can be achieved by this procedure even if the defect occurrence distribution is unknown. FIGS. 11(a) and 11(b) show clusters on a wafer and those on a chip, respectively.

Since it is highly possible that the defects in different clusters are caused by different causes, respectively, reinspection can be achieved without overlooking defects having a small occurrence probability when some of the defects in each cluster are visually reinspected. Such a function is very effective because a large number of defects of the same kind are liable to be formed in patterns. Even if the defects are classified automatically in clusters, the variation of the quality of the same process with time can be more accurately known by calculating an occurrence distribution function for each cluster and clustering is carried out in the next inspection on the basis of the calculated distribution function than by simply controlling the process only on the basis of the number of defects.

FIG. 12 shows an image of an occurrence probability distribution measuring wafer having intentionally formed sample defects. A method of determining an occurrence probability function for each cluster may automatically inspect the occurrence probability distribution measuring wafer having the intentionally formed sample defects as shown in FIG. 12, and may calculate an occurrence probability distribution function for detected defects included in each of the clusters arranged in predetermined regions. This method enables the omission of troublesome visual reinspection and the automatic classification of defects analogous with the sample defects.

FIG. 13 shows a pattern inspecting system in a second embodiment according to the present invention, in which the principal part of FIG. 1 is formed through a network. Shown in FIG. 13 are a defect detecting unit 41a which inspects a pattern and calculates defect characteristic quantities, a defect classifying and displaying unit 43 which classifies defects on the basis of defect characteristic quantities and displays the defects. In the second embodiment, the defect detecting unit 41a and the defect classifying and displaying unit 43 are connected by a local area network, and the defect detecting unit 41a transfers a defect data list to the defect classifying and displaying unit 43 when necessary. Usually, the defect detecting unit 41a must be installed in a clean room. When the defect classifying and displaying unit 43 is separated from the defect detecting unit 41a, the defect classifying and displaying unit 43 can be installed in other control room, which improves the facility for use of the pattern inspecting system. The defect detecting units 41b of a plurality of other pattern inspecting system can be connected to the defect classifying and displaying unit 43. If a reviewing apparatus 44 is connected to the same network, the sample defects sampled from the clusters for visual inspection can be directly sent from the defect classifying and displaying unit 43 to the reviewing apparatus 44 for the further efficient inquiry into the causes of defects.

The present invention exercises the following effects.

(1) Classification of defects and the results of inspection can be achieved substantially with the detection of the defects. Accordingly, visual reinspection using a reviewing apparatus is not necessary and inquiry into the causes of defects through the appearance inspection of defects can be quickly achieved.

(2) Since sample defects cam be sampled on the basis of the results of classification of the defects in clusters for visual reinspection using a reviewing apparatus, the possibility of overlooking critical defects which are formed at a low frequency can be reduced.

(3) Unmanned monitoring of the frequency of occurrence of defects classified in clusters is possible and therefore the variation of the quality of the semiconductor pattern forming process can be closely monitored.

What is claimed:

1. A method for defect clustering in inspection patterns on the surface of a workpiece, said method comprising the steps of:

(a) judging whether an occurrence probability distributions of clusters is known or not;

(b) carrying out the following steps (c) and (d), if the occurrence probability distributions of clusters are known, and carrying out the following steps from (e) to (j), if the occurrence probability distributions of clusters are not known;

(c) entering an occurrrence probability distributions of clusters; and (d) classifying the defects in clusters having the highest occurrence probability;

(e) calculating a distance between optional defects in a characteristic space;

(f) assuming that one defect forms one cluster respectively in an initial state;

(g) setting a threshold;

(h) combining some clusters in one cluster if the distance between nearest defects included in the clusters, is less than the threshold;

(i) increasing the threshold somewhat; and (j) repeating steps (h) and (i) until the threshold exceeds a predetermined upper limit or the number of the clusters in less than a predetermined lower limit.

* * * * *